United States Patent [19]
Pohl et al.

[11] Patent Number: 5,202,121
[45] Date of Patent: Apr. 13, 1993

[54] THROMBOLYTIC COMPOSITIONS

[75] Inventors: Gunnar Pohl, Odalvägen; Christer Mattsson, Rinkebyvägen, both of Sweden

[73] Assignee: Kabigen AB, Stockholm, Sweden

[21] Appl. No.: 459,210

[22] Filed: Dec. 29, 1989

[30] Foreign Application Priority Data

Jan. 10, 1989 [SE] Sweden ........................... 8900067

[51] Int. Cl.$^5$ ............................................. A61K 37/54
[52] U.S. Cl. ................................. 424/94.64; 424/94.2
[58] Field of Search ................. 424/94.63, 94.64, 94.2; 435/212, 219, 221

[56] References Cited

U.S. PATENT DOCUMENTS

| | | | |
|---|---|---|---|
| 4,935,237 | 6/1990 | Higgins et al. | 424/94.64 |
| 4,963,357 | 10/1990 | Bell et al. | 424/94.64 |

FOREIGN PATENT DOCUMENTS

| | | |
|---|---|---|
| 0223192 | 5/1987 | European Pat. Off. . |
| 241209 | 10/1987 | European Pat. Off. ......... 424/94.63 |
| 8704722 | 8/1987 | World Int. Prop. O. . |
| 8808451 | 11/1988 | World Int. Prop. O. . |

OTHER PUBLICATIONS

Kalyan, J. Biol. Chem., vol. 263, No. 8, (Mar. 15, 1988), 3971–8.
Pannell et al., J. Clin. Invest., vol. 81 (Mar. 1988), 853–9.
Verstraete et al., Blood, vol. 67, No. 6 (Jun. 1986), 1529–41.
Ann Rev. Med., (1988), vol. 39, pp. 405–423, "Thrombolytic Therapy" D. Collen, et al.

Primary Examiner—Jacqueline Stone
Attorney, Agent, or Firm—Oblon, Spivak, McClelland, Maier & Neustadt

[57] ABSTRACT

A thrombolytically active composition comprising in combination a modified tissue-type plasminogen activator (t-PA) as a major component and a normal human t-PA, Streptokinase or human urokinase as a minor component in a pharmaceutically acceptable excipient;
  a method of treating a thrombotic disorder; and
  a medicinal kit or package for use in treating thrombotic disorders.

16 Claims, 5 Drawing Sheets

THROMBOLYTIC COMPOSITIONS

The present invention relates to thrombolytically active compositions comprising useful combinations of thrombolytically active ingredients. The invention also covers a method for the preparation of such thrombolytically active compositions, a method of treating thrombotic disorders and a medicinal kit or package for use in such treatment.

BACKGROUND OF THE INVENTION

Vascular disorders, such as acute myocardial infarction, stroke, deep vein thrombosis, pulmonary embolism, peripheral arterial thrombosis or other thrombotic diseases are caused by partial or total occlusion of the blood vessel by a blood clot. In order to restore the blood flow the clot has to removed or degraded. The degradation of blood clots can be achieved by the use of plasminogen activators. Such activators are able to convert the plasma proenzyme plasminogen into its active form, plasmin. Plasmin efficiently degrades fibrin which is the main component of the clot.

The compounds which are presently available for thrombolytic treatment may be classified into three groups. Tissue-type plasminogen activators (t-PA), urokinase-type plasminogen activators (u-PA) and streptokinase. For the treatment of thrombosis they all have certain limitations. Streptokinase is a bacterial protein and induces an immunologic response which can cause clinical problems. Both u-PA and streptokinase lack fibrin selectivity and fibrin affinity. Intravenous administration of these activators generate plasmin systemically which may cause a haemorrhagic potential and bleeding complications. Tissue plasminogen activator has a high affinity for fibrin and is only efficiently activating plasminogen when it is bound to fibrin. Thus, t-PA can efficiently degrade the fibrin clot without causing systemic plasmin effects.

Recombinant DNA techniques as well as conventional biotechnical methods have been employed in order to produce t-PA for thrombolytic therapy [European Patent application number 93619, European Patent application number 41766 and European Patent Application number 178105]. Clinical studies with recombinant t-PA have shown that efficient thrombolysis requires doses of 80–100 mg. The high doses required may be related to the fact that t-PA is rapidly cleared from the circulation by the liver and the half-life of native t-PA in man is only a few minutes [Garabedian et al. 1986, Am. J. Cardiol. 58, pp 673–679]. The short half-life also makes it necessary to administer the activator as a continuous infusion over several hours instead as a more convenient and faster bolus injection.

Therefore, attempts have been made to generate plasminogen activators with high fibrin affinity and fibrin selectivity having also an extended half-life in the blood. It is anticipated that such plasminogen activators will be effective at lower doses than what is presently used for t-PA and that bolus injection could be used instead if infusion.

Genetically modified variants of t-PA having an extended in vivo half-life have been produced by recombinant DNA techniques [European Patent Applications 88850207.7 and 242836 and International Patent Application PCT number WO 87/04722]. Animal tests with such modified t-PA molecules have shown that slower clearance is associated with a more efficient thrombolysis [Collen et al. 1988, Blood 71, 216–219;].

However, when the variants are tested in vitro for their ability to lyse human blood clots the activity is associated with a marked lag-phase [Kalyan et al. 1988, J. Biol. Chem. 263, 3971–3978]. This lag-phase reduces the activity of the variant and increases the lysis time, thus counteracting the benefits of a longer half-life in vivo.

DEFINITIONS

In this application the plasminogen activator nomenclature proposed at the XXVIII Meeting of the International Committee on Thrombosis and Haemostasis, Bergamo, Italy, Jul. 27, 1982, is used. Tissue-type plasminogen activator (t-PA) and urokinase-type plasminogen activator (u-PA).

The terms "normal t-PA" or "t-PA" is used in the present application to describe the full sized human t-PA having the amino acid sequence as deduced from the cDNA described by Pennica et al. 1983, Nature, 301, 214–221. Preparations of naturally ocurring t-PA have been found to display three different N-terminal amino acid residues. The longest form (L-form) has glycine (Gly) as the first residue, whereas short (S-form) or uterine (U-form) forms have serine (Ser) and valine (Val) as the N-terminal amino acid residue. All these different forms of t-PA have the characteristics of normal t-PA.

The term "t-PA variants" denotes various forms of normal t-PA which have been modified in order to reduce the fast clearance rate which is characteristic for normal t-PA.

DESCRIPTION OF THE INVENTION

It has now been found that the addition of small amounts of normal (recombinant or non-recombinant) t-PA, u-PA or streptokinase to modified t-PA preparations removes the lag-phase in the thrombolytic activity of these compounds and the resulting activity is increased to the level of normal t-PA. Taking into consideration the significantly prolonged half-life of the modified t-PA molecules in vivo the improved activity of the mixture will cause a significant synergistic effect and thereby create a faster and more efficient thrombolytic effect than any of the compounds when taken alone.

The present invention is based on the observation that t-PA variants which have been modified as to increase the in vivo half-life display a lag-phase with regard to the onset of thrombolytic activity. In contrast, normal t-PA, streptokinase or urokinase does not show such lag-phase. This lag-phase is not observed if the mutant material is mixed with a minor fraction of normal t-PA, urokinase or streptokinase. When these agents are present in amounts which does not cause significant thrombolysis alone (sub-thrombolytic concentrations), the activity of the t-PA variants is not associated with a significant lag-phase. Furthermore, it has been found that clots which have been incubated with low concentrations of normal t-PA, then washed followed by a new incubation with the t-PA variant, are rapidly lysed similarly as when the variant and normal t-PA were incubated together.

This indicates that a thrombus may be "primed" with an injection of normal t-PA and then efficiently lysed by a second injection of a t-PA variant with an extended plasma half-life. With such combination treatment the thrombotic patient can be "primed" with a safe, sub-thrombolytic, injection of t-PA, u-PA or streptokinase already before entering into the hospital where further infusions with an efficient t-PA mutant may complete the thrombolytic treatment. The advantages with the combination therapy outlined above is that a shorter time is required from start of treatment to the lysis of the thrombus. Especially in the case of acute myocardial infarction, rapid thrombolysis is important for myocardial salvage. Another advantage with the combination treatment, either if the two agents are used in a mixture or if they are used separately, is that efficient thrombolysis can be achieved at a total dose which is significantly lower than the dose of t-PA used to day.

The invention is based on the findings described above. In one aspect, it provides a thrombolytically active pharmacological composition comprising a synergistic combination of t-PA, or u-PA or streptokinase as the minor component and a fibrinolytically active t-PA variant as the major component, preferably in admixture with a pharmaceutically acceptable excipient.

In another aspect, the invention provides a method of preparing a thrombolytically active pharmaceutical composition, comprising a combination of t-PA or u-PA or streptokinase as the minor component and a fibrinolytically active variant of t-PA as the major component in a pharmaceutically acceptable excipient or excipients. The resulting pharmaceutical composition may have any appropriate form but is preferably in the form of an intravenous infusion or injection fluid.

The minor component, being t-PA, u-PA or streptokinase, may be of any conventional kind obtained from any suitable source. In the experiments described herein the t-PA is obtained from the conditioned medium of a melanoma cell line and the streptokinase is from a natural strain of streptococcus, but t-PA, u-PA or streptokinase derived from natural sources or from genetically engineered eukaryotic or prokaryotic cells will be equally adequate.

The major component of the combination treatment is a plasminogen activator, preferably a modified t-PA variant, which is characterized by a longer in vivo half life and by a lag-phase in the in vitro thrombolytic activity when compared with the normal t-PA. The t-PA variants in the experiments to be described are produced by recombinant techniques in mammalian cells, but any plasminogen activator having the characteristics noted above obtained from natural sources or from genetically ingineered eukaryotic or prokaryotic cells will also be adequate. For details concerning useful t-PA variants for use in the compositions of the present invention reference is made to published European patent application 88850207.7. In said European patent application there are described fibrinolytically active plasminogen activators of the tissue type which have longer biological half-life in vivo. The full disclosure of said application is incorporated herein by reference thereto. The main features of the variants described therein are summarized below.

The t-PA variants disclosed in European patent application 88850207.7 are characterized in that in addition to the growth-factor domain (G-domain) also the first kringle domain (K1-domain) has been deleted. Additionally the plasminogen activator of the invention has been modified in one or more of the following sites or region: the sites of amino acid residues 177, 184, 277 and 448, and the finger domain (F-domain), if modified, being deleted in part or all of it.

It is preferred that the F-domain, optionally, has been deleted and the glycosylation site at residue 184 has been modified to prevent glycosylation thereat. It is particularly preferred that both sites 184 and 448 have been modified to prevent glycosylation at said sites.

In this disclosure, when referring to modification of glycosylation sites 184 and 448, the modification is such that no glycosylation occurs. Thus, the site in question is modified as to prevent N-glycosylation by modifying the N-glycosylation consensus sequence.

In a particularly preferred embodiment, the F-domain has been deleted altogether and the amino acids at sites 184 and 448 have been modified to prevent glycosylation at said sites.

In such plasminogen activator it is preferred that the additional modification has been made at the site of amino acid residue 277, and such modification can be in the form of change to an amino acid residue which in its side chain does not exhibit a positive charge. An example of such modification is substituting a valine residue for the lysine residue at the 277 site.

In another preferred embodiment the additional modification has been made in the K1 domain, either as the only modification of the molecule in addition to the modification of the growth-factor domain or in combination with the modification of the site of amino acid residue 277.

In yet another embodiment, the modification of the molecule has been made at the site of amino acid residue 184, whereby N-glycosylation at said site, which occurs in normal t-PA, is no longer achievable. In such a modification at the 184 site the asparagine residue thereof can be replaced by a glutamine residue.

In addition to the said modifications at amino acid sites 184 and 277 it is also preferred to modify the K1 domain, optionally in combination with a modification of the F-domain.

All such modifications of the different domains can be constituted by deletion of part or all of the respective domains.

Several methods for the purification of t-PA, u-PA, streptokinase and t-PA mutants are available. Usually a number of chromatographic steps are employed.

The weight ratio between the minor and the major component of the combination treatment may vary, but the minor component is always less than 50% by weight of the total dose given. The preferred weight ratio for the minor component is about 5 to about 30% of the total dose and a particularly preferred range is about 10 to about 20%.

Pharmaceutical compositions containing a mixture of the components or containing the components separately may have any form suitable for administration to man. The preferred form is an intravenous injection or infusion fluid or a combination of such fluids. Such fluids may contain the active substances at a concentration of 0.1 to 10 mg/ml.

The total doses for the combination treatment as described in this invention for administration to a thrombotic patient may be significantly lower than required for t-PA or u-PA alone. Due to the reduced lag-phase in activity the combination will induce faster and more efficient thrombolysis than if the t-PA variant was used alone.

Thus, in summary, the invention relates to a thrombolytically active composition comprising in combination a modified tissue-type plasminogen activator (modified t-PA) as a major component and a normal human t-PA, streptokinase or human urokinase as a minor component in a pharmaceutically acceptable excipient.

It is preferred that the minor component constitutes up to about 30% of the combined weight of said two components. When reference is made to "major component" and "minor component" the meaning is that the major component constitutes more than 50% by weight of the combined weight of said components, whereas the minor component constitutes less than 50% by weight of said combined weight.

In such thrombolytically active composition according to the invention it is particularly preferred to use a combination of modified t-PA and normal human t-PA.

The invention also covers a method for the preparation of a thrombolytically active composition, and said method involves the measure of combining a modified tissue-type plasminogen activator (modified t-PA) as a major component and normal human t-PA, streptokinase or human urokinase as a minor component in a pharmaceutically acceptable excipient.

Furthermore, the invention includes a method of treating thrombotic disorder, said method comprising administering to a patient suffering from such disorder a thrombolytically effective amount of the composition as described above.

According to an alternative method for treating thrombotic disorder the following steps are included:
a) administering to a patient suffering from such disorder by an initial injection normal human t-PA, streptokinase of human urokinase in an amount up to about 30 mg; and then
b) administering to the same patient by a second injection a thrombolytically effective amount of a modified t-PA.

Finally, the invention relates to a medicinal kit or package for use in treating thrombotic disorders, said kit or package containing:
a) normal human t-PA, streptokinase or human urokinase in a minor amount in a pharmaceutically acceptable excipient;
b) a modified t-PA in a thrombolytically effective amount in a pharmaceutically acceptable excipient; and
c) written instructions for simultaneous or consecutive administration of the compositions under a) and b) in said order to a patient suffering from such disorder.

In such medicinal kit or package it is preferred that component a) contains up to about 10 mg, such as about 1 to about 10 mg, of active ingredient, and component b) contains up to about 50 mg, such as about 10 to about 50 mg, of active ingredient.

The invention will be illustrated further in the following by non-limiting specific examples which are purely exemplary and should not be construed as limiting the scope of the present invention as defined in the appended claims. This illustration will be made with reference to the appended drawings, wherein:

Figure 4:
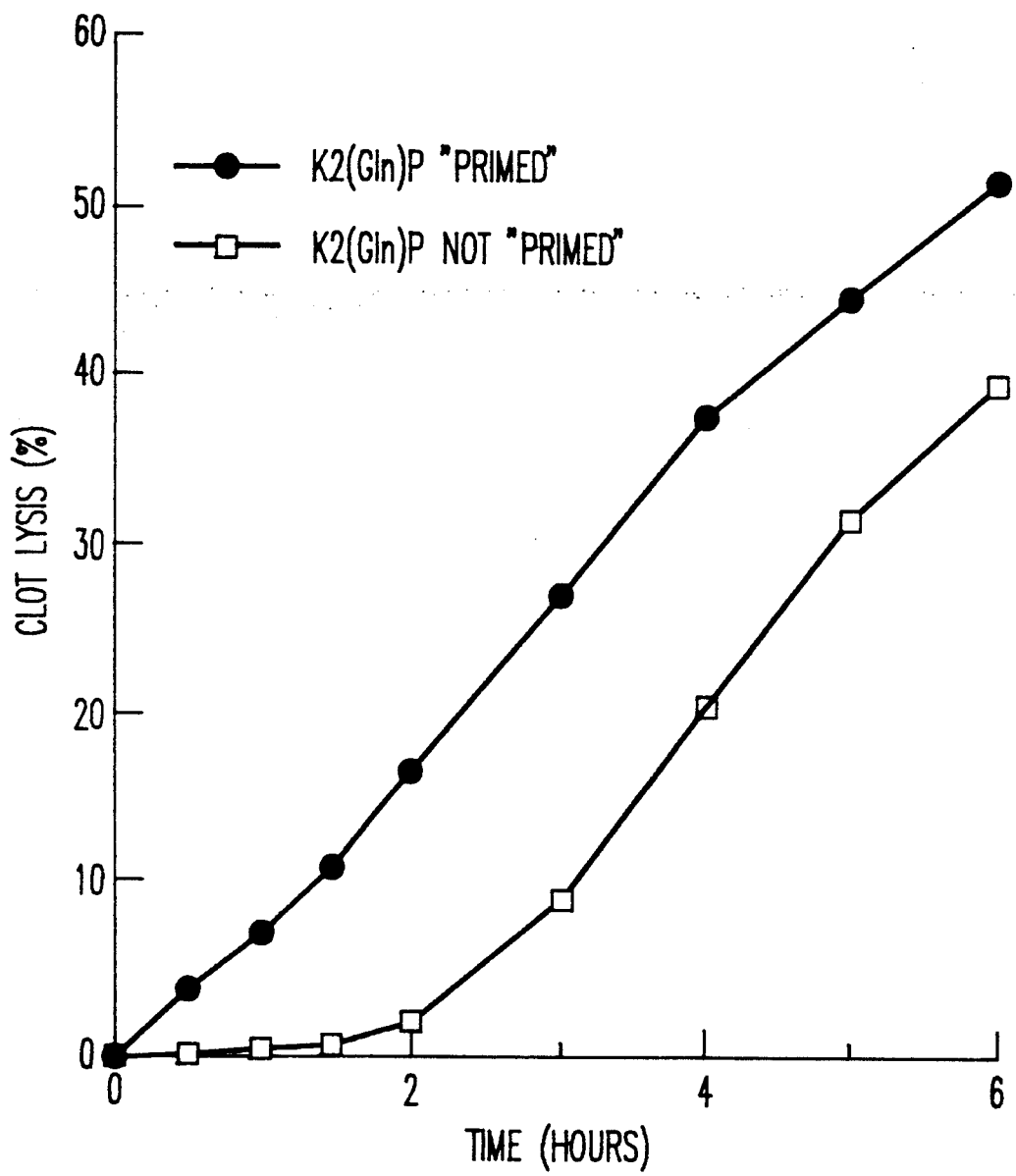

FIG. 4 shows the in vitro thrombolytic activity of the t-PA variant K2(Gln)P acting on a human blood clot which has first been incubated with normal t-PA (50 ng/ml) for 30 minutes ("primed"), then washed and transferred to a second solution containing 500 ng/ml of the t-PA variant. The thrombolytic activity was also determined after the clot has been pre-incubated in the absence of t-PA ("not primed").

Figure 5:
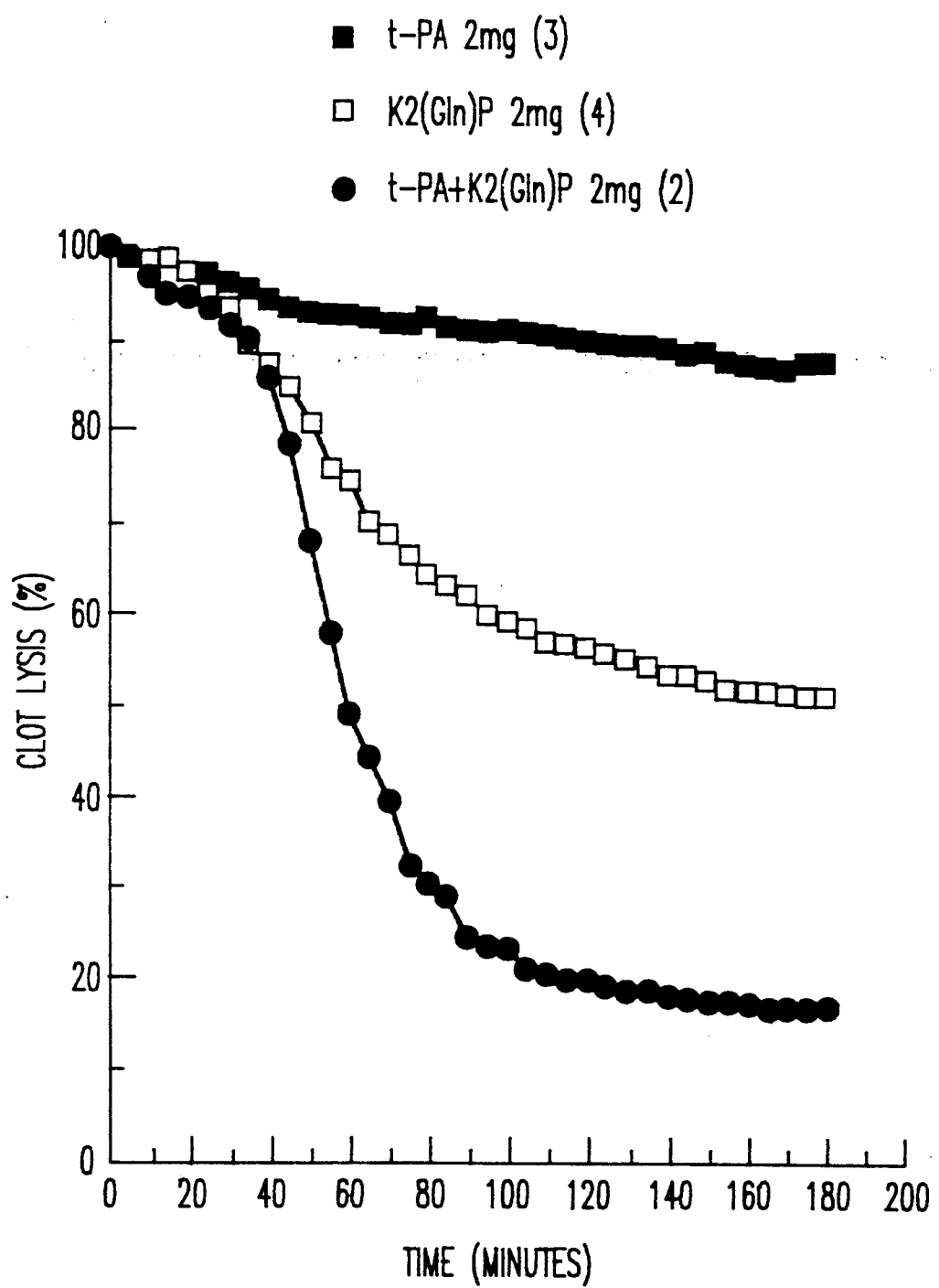

FIG. 5 shows the in vivo thrombolytic activity in rabbits of 2 mg of t-PA, the t-PA variant, K2(Gln)P and a 1:4 mixture of t-PA and K2(Gln)P. The experimental conditions are detailed in Example 4.

EXAMPLE 1

This experiment demonstrates the effect of a low concentration of t-PA on the in vitro thrombolytic activity of a t-PA mutant.

The t-PA used is obtained from human melanoma cells. The t-PA variant molecule, denoted "K2(Gln)P", is a deletion mutant which differs from the normal human t-PA molecule as follows. Residues no. 6-173 are deleted, and Asn177 and Asn184 are changed to Ser and Gln respectively. This mutant displays an in vivo plasma half-life of about 50 minutes when tested in rabbits. The corresponding value for normal t-PA is about 3 minutes. The construction of expression vectors and the expression of t-PA mutants such as "K2(Gln)P" in mammalian cells have been described in patent application EPO 88850207.7.

The Chandler's loop circulation system was used to determine the in vitro thrombolytic properties of t-PA, "K2(Gln)P" and the combination. For the details of the procedures we refer to C. Mattsson et al., Thrombosis Research 21, (1981) 535-545. Briefly, human blood was drawn in sodium citrate, centrifuged, mixed with $^{125}$I-fibrinogen and filled into a Tygon plastic tubing. The plasma was recalcified with $CaCl_2$ and the tubing ends were connected to form a circle. The circular tube was rotated on a titled turntable for 24 hours to allow the clot to form before the addition of the various plasminogen activators. Samples were drawn from the tubing and assayed for radioactivity at regular time intervals and the radioactivity released from the clot was expressed as % clot lysis.

Figure 1:
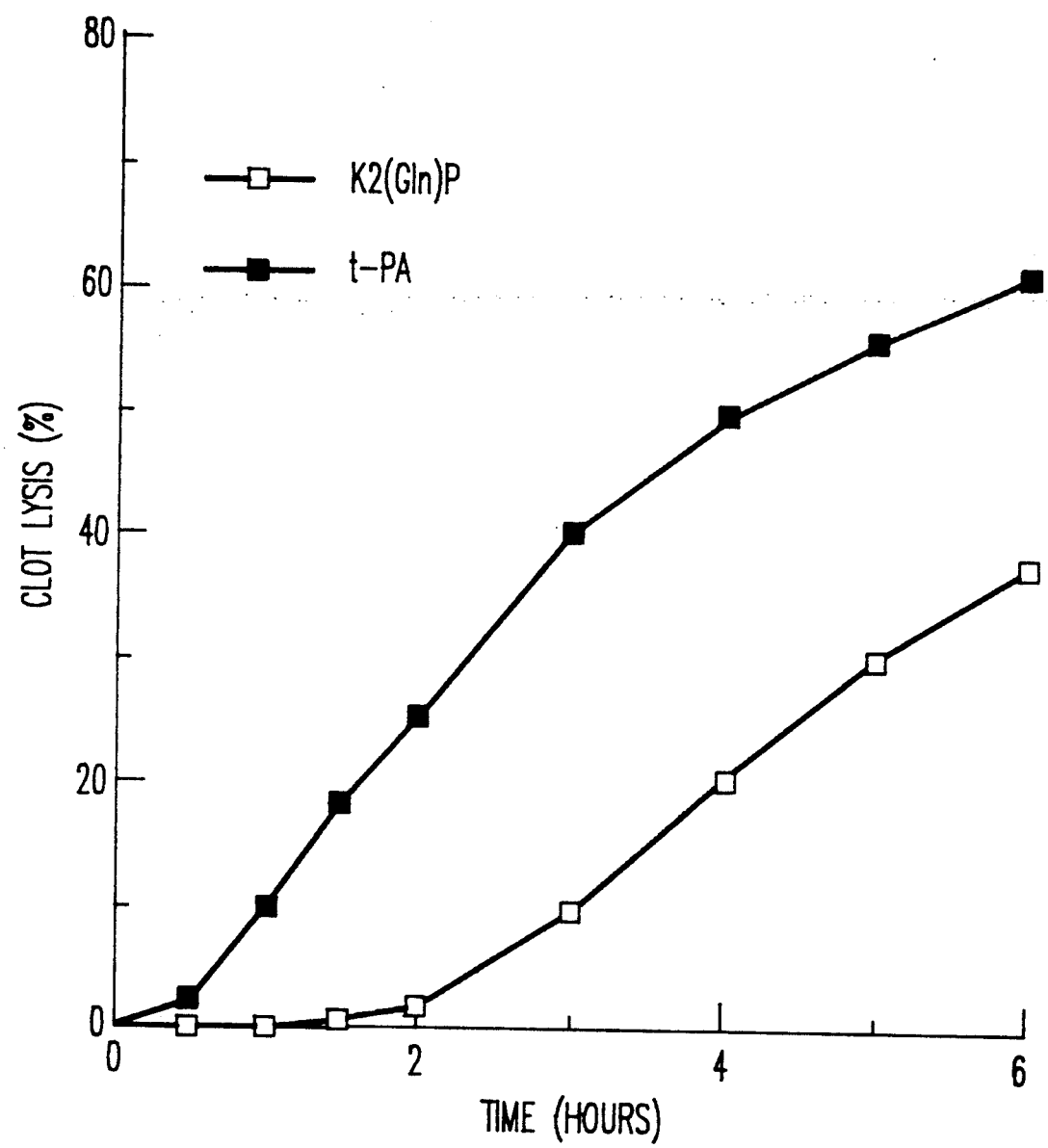
FIG. 1 shows the dissolution of a human plasma clot in vitro as a function of time. The reaction is started by the addition of 500 ng/ml of normal human (melanoma) t-PA (t-PA) or 500 ng/ml of the t-PA variant K2(Gln)P.
Figure 2:
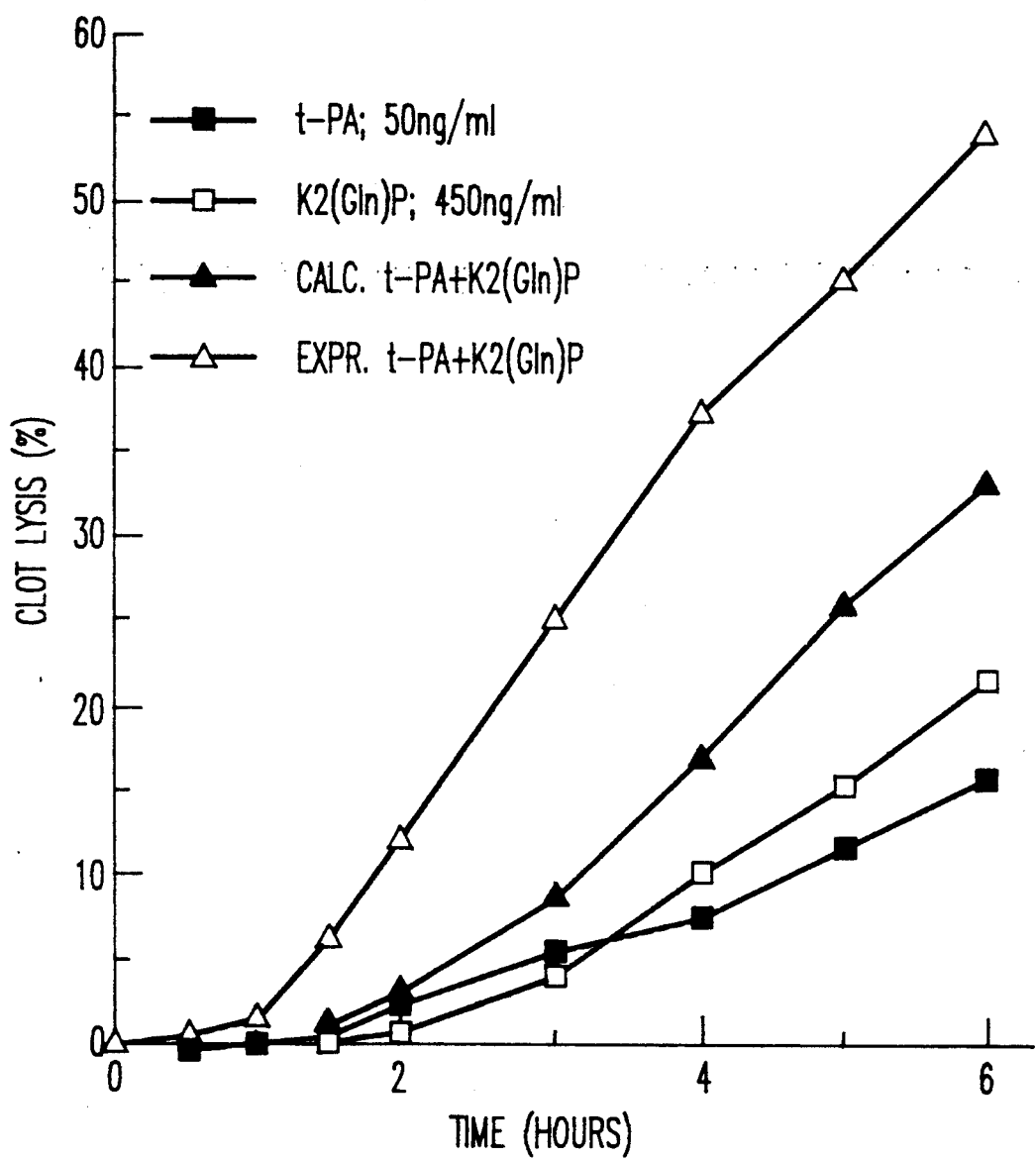
FIG. 2 shows the in vitro thrombolytic effect of t-PA (50 ng/ml), the t-PA variant K2(Gln)P (450 ng/ml), the calculated sum of the activity of the two compounds, and the experimentally found activity of the two compounds when mixed.
Figure 3:
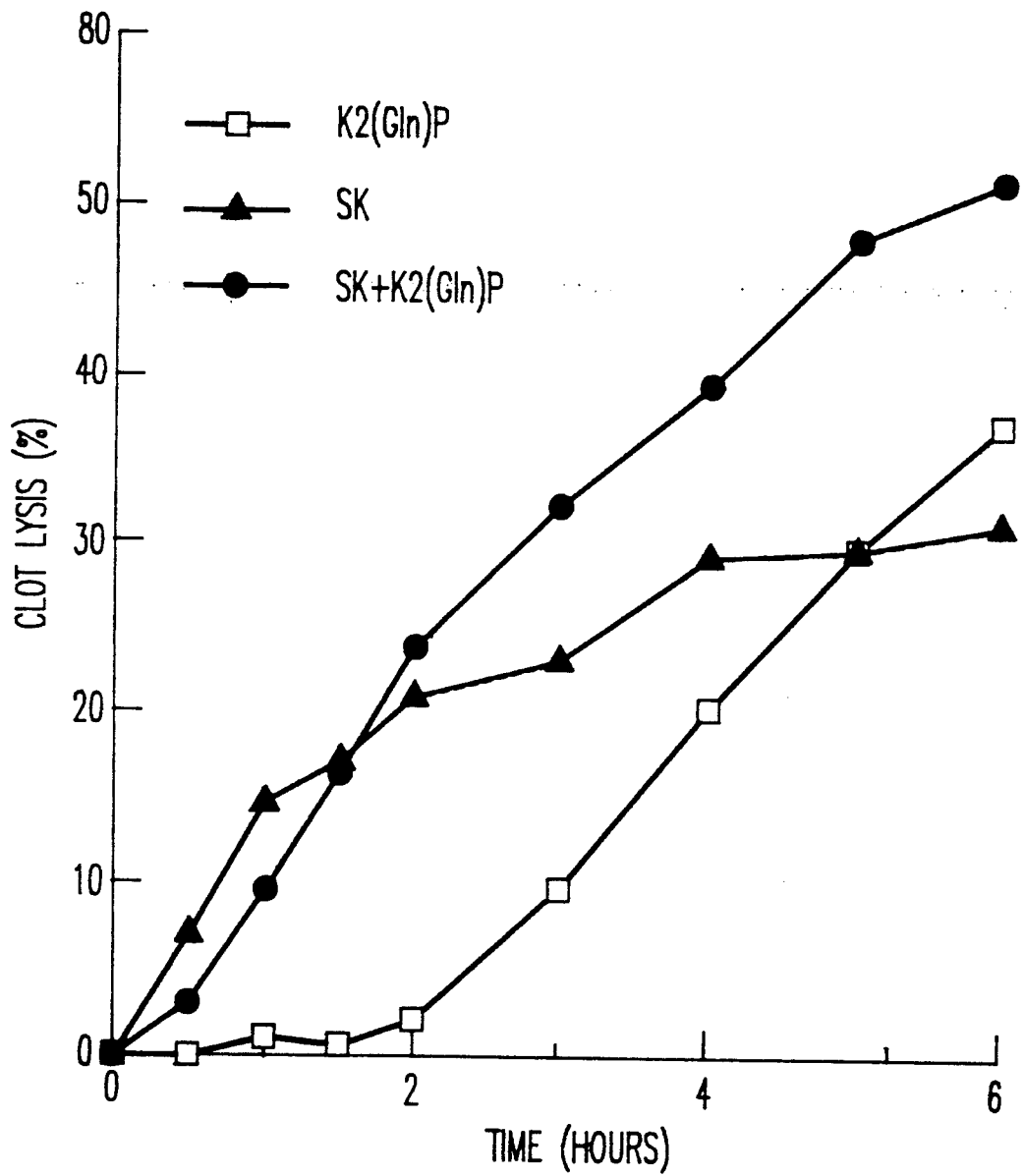
FIG. 3 shows the in vitro thrombolytic activity of 500 ng/ml of streptokinase (SK), 500 ng/ml of the t-PA variant K2(Gln)P, and a mixture of the two containing 100 ng/ml of SK and 400 ng/ml of K2(Gln)P.

The results of such experiments performed with t-PA and "K2(Gln)P" is shown in FIGS. 1 and 2 respectively. It can be seen that t-PA induces thrombolysis immediately after injection whereas in the case of "K2(Gln)P" the activity displays a marked lag-phase and essentially no activity is seen before one hour. However, by combining a low dose dose of t-PA (50 ng/ml) with 450 ng/ml/ml of K2(Gln)P much of the lag-phase of the t-PA variant is abolished (FIG. 3). The activity obtained for the mixture (expr. t-PA+K2(Gln)P) is significantly higher than can be calculated from the activity of the two compounds alone as seen for the curve "calc. t-PA+K2(Gln)P".

EXAMPLE 2

This experiment demonstrates that the lag-phase of in vitro thrombolytic activity seen for the t-PA variant can be abolished if the blood clot first is subjected to low amounts of t-PA. Thus, the thrombus may be "primed" by t-PA and subsequently efficiently lysed by a t-PA variant which has an extended in vivo half-life. The experiment was performed as in experiment 1 with the following exception. The plasma clots were first incubated for 1 hour in a t-PA containing (50 ng/ml) solution before they were washed and transferred into a loop containing K2(Gln)P at a concentration of 500 ng/ml (FIG. 4). No clot lysis occurred when the "primed" and washed clot was incubated for 6 hours without added t-PA variant.

EXAMPLE 3

This experiment demonstrates that a synergistic in vitro thrombolytic effect is obtained when streptokinase and the t-PA variant K2(Gln)P is mixed at proper ratio and also that the lag-phase in activity for K2(Gln)P is abolished when streptokinase is included.

Mixtures of K2(Gln)P and streptokinase, 400+100 ng/ml are compared with 500 ng/ml of the two compounds alone (FIG. 3). A marked synergistic effect is seen in this system since the 400+100 ng/ml mixture of K2(Gln)P and streptokinase is 40-65% more effective than any of the compounds alone.

EXAMPLE 4

This experiment demonstrates the synergistic thrombolytic effect of a mixture of the t-PA variant K2(Gln)P and normal t-PA in rabbits.

The thrombolytic effect in vivo was evaluated in a rabbit jugular vein thrombosis model. The jugular vein of a pentobarbitone anaesthetized rabbit was uncovered and all tributaries were ligated. A 2 cm long segment of the jugular vein was ligated and the enclosed blood was removed and exchanged with the same volume of freshly collected human whole blood, mixed with trace amounts of $^{125}$I-human fibrinogen and thrombin. A cotton thread, around which the radiolabelled clot will be formed, was then inserted through the vessel in order to avoid embolization. After clot formation (about 15 minutes) the surgical clamps were removed and saline was flushed over the clot in order to restore a certain degree of flow over the clot and to remove non-clottable $^{125}$I-fibrinogen from the clot surroundings.

The rate of thrombolysis was continuously monitored with a flat surface gamma detector probe, (Alnor Instruments, Studsvik, Sweden) which was secured about 1 cm above the clot. The plasminogen activators were injected as a bolus dose into the contralateral marginal ear vein and gamma counts were measured for 30 seconds every fifth minute during three hours.

The results of such an in vivo experiment is shown in FIG. 5 where a total amount of 2 mg plasminogen activator was injected into rabbits weighing 3 kg. The thrombolytic agents were: a) normal t-PA, b) t-PA variant K2(Gln)P and c) a 1:4 mixture of t-PA and the variant. A dramatic synergistic effect is obtained when normal t-PA and the t-PA variant is injected as a mixture. The mean percentage clot lysis after 3 hours is 12, 45 and 83 for normal t-PA, K2(Gln)P and the mixture respectively.

From the experiments above we conclude that a combined administration, either as a mixture or consecutively, of t-PA and t-PA variants with a prolonged plasma half-life to human patients will induce efficient thrombolysis at doses significantly lower than normally used for each of the agents used alone.

We claim:

1. A thrombolytically active composition comprising in combination a modified tissue-type plasminogen activator (modified t-PA) having an extended biological half-life and exhibiting a lag phase with respect to in vitro thrombolytic activity when compared with normal t-PA as a major component and a normal human t-PA, or streptokinase as a minor component in a pharmaceutically acceptable excipient.

2. A thrombolytically active composition according to claim 1, wherein the minor component constitutes up to about 30% of the combined weight of said two components.

3. A thrombolytically active composition according to claim 1, wherein the modified t-PA is used in combination with normal human t-PA.

4. A thrombolytically active composition according to claim 1 which is in a fluid form suited for infusion or injection.

5. A thrombolytically active composition according to claim 4, wherein said components are present at a concentration of about 0.1 to about 10 mg/ml.

6. A method for the preparation of a thrombolytically active composition, comprising the step of combining a modified tissue-type plasminogen activator (modified t-PA) having an extended biological half-life and exhibiting a lag phase with respect to in vitro thrombolytic activity when compared with normal t-PA as a major component and normal human t-PA, or streptokinase as a minor component in a pharmaceutically acceptable excipient.

7. A method according to claim 6, wherein said modified t-PA is combined with normal human t-PA.

8. A method of treating a thrombotic disorder, which comprises administering to a patient suffering from such disorder a thrombolytically effective amount of the composition according to claim 1.

9. A method of treating a thrombotic disorder comprising the steps of:
   a) administering to a patient suffering from such disorder by an initial injection normal human t-PA, or streptokinase in an amount of up to about 30 mg; and then
   b) administering to the same patient by a second injection or by infusion a thrombolytically effective amount of a modified t-PA having an extended biological half-life and exhibiting a lag phase with respect to in vitro thrombolytic activity when compared to normal t-PA.

10. A medicinal kit or package for use in treating thrombotic disorders, containing:
    a) normal human t-PA, or streptokinase urokinase in a minor amount in a pharmaceutically acceptable excipient; and
    b) a modified tissue-type plasminogen activator (modified t-PA) having an extended biological half-life and exhibiting a lag phase with respect to in vitro thrombolytic activity when compared to normal t-PA in a thrombolytically effective amount in a pharmaceutically acceptable excipient; and
    c) written instructions for simultaneous or consecutive administration of the compositions under a) and b) in said order to a patient suffering from such disorder.

11. A medicinal kit or package according to claim 10, wherein component a) contains up to about 10 mg of active ingredient, and wherein component b) contains up to about 50 mg of active ingredient.

12. A medicinal kit or package according to claim 11, wherein component a) contains about 1 to about 10 mg of active ingredient and wherein component b) contains about 10 to about 50 mg of active ingredient.

13. A thrombolytically active composition according to claim 1, wherein said modified t-PA is K2(Gln)P.

14. A thrombolytically active composition according to claim 1, wherein said minor component is normal human t-PA.

15. A thrombolytically active composition according to claim 1, wherein said minor component is normal streptokinase.

16. A thrombolytically active composition comprising in combination, a modified tissue-type plasminogen activator (modified t-PA) having an extended biological half-life and exhibiting a lag phase with respect to in vitro thrombolytic activity when compared with normal t-PA as a major component, wherein said modified t-PA comprises t-PA wherein the G-domain, K-1 domain and at least a portion of the F-domain are deleted and wherein amino acid residue numbers 177, 184, 277 or 448 are modified to prevent glycolysation, and a normal human t-PA or streptokinase as a minor component, in a pharmaceutically acceptable excipient.

* * * * *

UNITED STATES PATENT AND TRADEMARK OFFICE
CERTIFICATE OF CORRECTION

PATENT NO. : 5,202,121
DATED : April 13, 1993
INVENTOR(S) : Gunnar POHL, et al.

It is certified that error appears in the above-indentified patent and that said Letters Patent is hereby corrected as shown below:

Column 1, line 61, "used instead if" should read --used instead of--.

Column 3, line 13, "t-PA used to day." should read --t-PA used today.--;
line 49, "ingineered" should read --engineered--.

Column 6, line 11, "the clot has been" should read --the clot had been--.

Column 7, line 50, "The results...is shown" should read --The results...are shown--.

Column 8, line 39, "initial injection normal human" should read --initial injection of normal human--;
line 50, "or streptokinase urokinase" should read --or streptokinase--.

Signed and Sealed this

Twenty-eight Day of February, 1995

Attest:

BRUCE LEHMAN

Attesting Officer    Commissioner of Patents and Trademarks